US00PP27067P3

(12) United States Plant Patent
Pineda

(10) Patent No.: US PP27,067 P3
(45) Date of Patent: Aug. 16, 2016

(54) ***THUJA* PLANT NAMED 'MONRIG'**

(50) Latin Name: *Thuja standishii×plicata*
Varietal Denomination: MonRig

(71) Applicant: Rigoberto Pineda, Salem, OR (US)

(72) Inventor: Rigoberto Pineda, Salem, OR (US)

(73) Assignee: Monrovia Nursery Company, Azusa, CA (US)

( * ) Notice: Subject to any disclaimer, the term of this patent is extended or adjusted under 35 U.S.C. 154(b) by 100 days.

(21) Appl. No.: 14/120,543

(22) Filed: Jun. 2, 2014

(65) Prior Publication Data

US 2015/0351298 P1 Dec. 3, 2015

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

PUBLICATIONS

Monrovia Horticultural Craftsmen Since 1926, Tiny Tower Arborvitae, 2015, retrieved on Nov. 5, 2015, retrieved from the Internet at <http://www.monrovia.com/plant-catalog/plants/5204/tiny-tower-arborvitae/> 1 p.*

* cited by examiner

*Primary Examiner* — June Hwu
(74) *Attorney, Agent, or Firm* — Cassandra Bright

(57) ABSTRACT

A new and distinct *Thuja* cultivar named 'MonRig' is disclosed, characterized by distinctive Yellow-Green and Green foliage, which changes to chocolate brown in the Winter. Plants have distinctive tight, upright growth habit. The new cultivar is a *Thuja*, suitable for ornamental garden purposes.

2 Drawing Sheets

Latin name of the genus and species: *Thuja standishii×plicata.*

Variety denomination: 'MonRig'.

BACKGROUND OF THE INVENTION

The new cultivar is a product of chance discovery by the inventor. This new variety, hereinafter referred to as 'MonRig', was discovered as a naturally occurring, whole plant mutation by the inventor, Rigoberto Pineda. The interesting new mutation was discovered in a commercial nursery in Dayton, Oreg. among a population of unpatented *Thuja standishii×plicata* during June of 2010.

After identifying the new variety as a potentially interesting selection, the inventor first organized propagation of 'MonRig' by meristem tissue culture at the same commercial laboratory during December of 2010. The inventor continued controlled testing and propagation, assessing stability of the unique characteristics of this variety. At least five generations have been reproduced and have shown that the unique features of this cultivar are stable and reproduced true to type.

SUMMARY OF THE INVENTION

The cultivar 'MonRig' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MonRig' These characteristics in combination distinguish 'MonRig' as a new and distinct *Thuja* cultivar:

1. Unique color of foliage: Youngest new foliage is yellow-green, changing to green. Foliage is chocolate brown in the Winter.
2. Distinctive tight, compact growth.
3. Distinctive upright branching.

COMPARISON TO PARENT VARIETY

'MonRig' is similar in most horticultural characteristics to the parent variety *Thuja standishii×plicata*. Plants of the new cultivar 'MonRig' however, grow more slowly, and are more compact with more upright branching. Additionally, the parent variety does not have chocolate brown winter foliage.

COMMERCIAL COMPARISON

*Thuja* 'MonRig' can be compared to the commercial variety *Thuja* 'MonPin', U.S. Plant Pat. No. 25,363. Plants are similar in most horticultural characteristics, however, plants of the new variety differ in the following:

1. 'MonRig' grows faster achieving approximately 150 cm in height in the same amount of time 'MonPin' grows to approximately 75 cm.
2. Winter foliage color of 'MonRig' is near RHS Grey-Brown N199C, tinged N199D. Winter foliage color of 'MonPin' is darker yellow with orange red tips.
3. Immature foliage of the new variety is color near Yellow-Green 151B, immature foliage of 'MonPin' is colored near Yellow-Orange 15C.

BRIEF DESCRIPTION OF THE PHOTOGRAPHS

Figure 1:
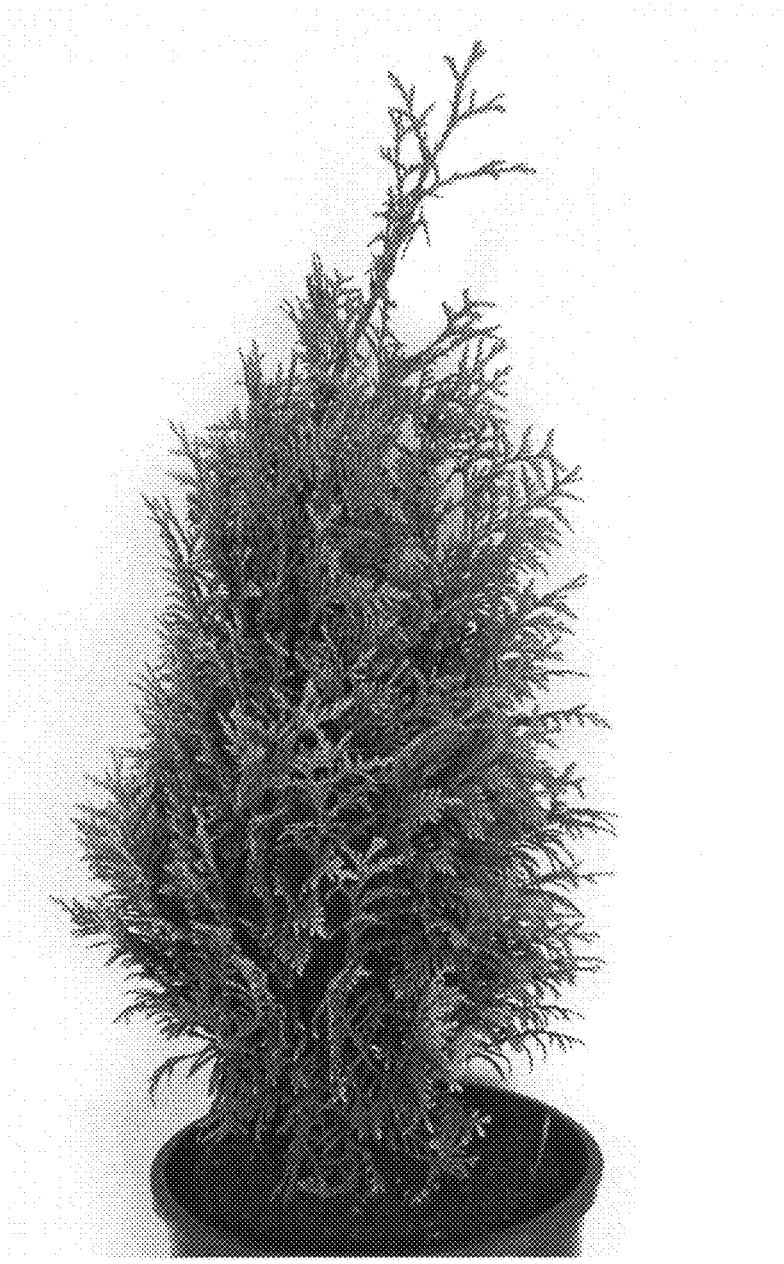

The accompanying photograph in FIG. 1 illustrates in full color a typical plant of 'MonRig' grown outdoors in Magnolia, Tex.. The plant is approximately 2 years old, and is shown in a three gallon container.

Figure 2:
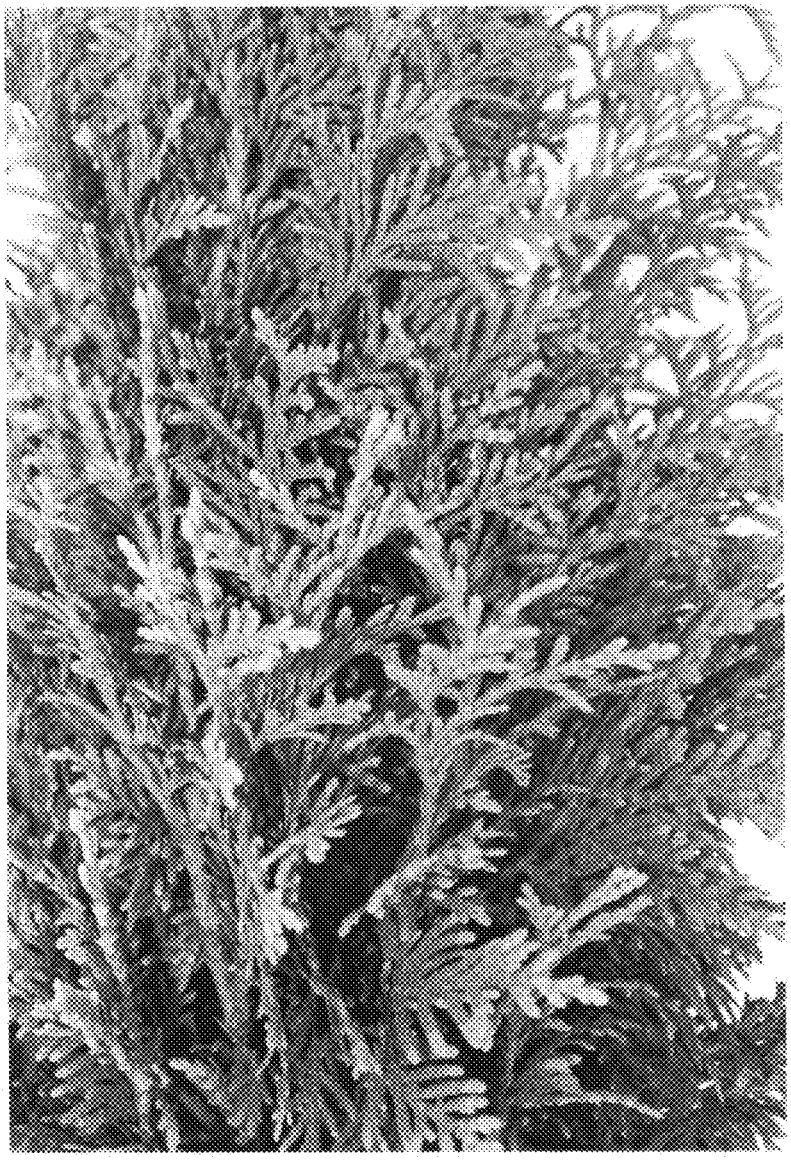

FIG. 2 shows a close up of typical foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MonRig' plants grown outdoors in Dayton, Oreg. Plants are approximately 2 years old, in a 3 gallon nursery container. Measurements and numerical values represent averages of typical plant types.

Botanical classification: *Thuja standishii×plicata* 'MonRig'.

PROPAGATION

Time to rooting: 60 to 90 days at approximately 40-50° F.

Root description: Fibrous, very well branched. Colored near RHS Brown 200C.

PLANT

Growth habit: Tightly pyramidal to conical, uniform appearance.

Height: Approximately 152 cm. after 4 years.

Plant spread: Approximately 56 cm. after 4 years.

Typical growth rate: Moderate for species.

Pinching Required: Yes.

*Details of pinching*.—Light shearing to maintain shape.

Branching characteristics: Branching arrangements. Alternate, main stem is upright with numerous (approximately 40) secondary branches. Lateral stems are held at an angle of 45 degree with flat sprays extending upward.

Length of lateral branches: Approximately 18 cm.

Branch density: Dense.

Average number of lateral branches: Approximately 5 main branches, approximately 40 secondary branches.

Diameter of lateral branches: Approximately 0.5 cm.

Lateral branch shape in cross section: Generally oval.

Lateral branch strength: Flexible.

Lateral branch color: Near RHS Greyed-Orange 177B.

Lateral branch texture: Scaly and soft to the touch. Scales colored near Greyed-Orange 177C and 177D.

Internode length: Approximately 4.5 cm on average of main stem approximately 3 cm on average approaching the tip.

Lenticels present: No.

FOLIAGE

General description: Tightly held, scale like leaves on planar branchlets.

Leaf:

*Arrangement*.—Opposite.

*Type*.—Scale.

*Shape of blade*.—Awl shaped.

*Average length*.—Approximately 0.25 cm.

*Average width*.—Approximately 0.15 cm.

*Apex*.—Acute.

*Base*.—Truncate.

*Attachment*.—Sessile.

*Margin*.—Entire.

*Texture of top surface*.—Glabrous.

*Texture of bottom surface*.—Glabrous.

*Leaf internode length*.—Leaves touching, overlapping as younger leaves emerge above older foliage.

*Color*.—Young foliage upper side: Near R.H.S. Yellow-Green 151B. Young foliage under side: Near R.H.S. Yellow-Green 151B. Mature foliage upper side: Near R.H.S. Green 137A. Mature foliage under side: Near R.H.S. Green 137A. Winter foliage upper side: Near R.H.S. Grey-Brown N199C, tinged N199D. Winter foliage under side: Near R.H.S. Grey-Brown N199C, tinged N199D.

*Venation*.—Linear, indistinguishable from leaf blade.

*Durability of foliage to stresses*.—Flexible and resistant to breakage.

*Fragrance*.—Strong, pleasant cedar foliage-like scent.

*Other foliage characteristics*.—Leaf glands and leaf stomata not observed.

Branchlets: Completely covered by leaves. Dissected into 2 or 3 sub-branchlets.

*Average length*.—Approximately 7.5 cm.

*Average width*.—Approximately 3.5 cm.

*Density of leaves*.—Approximately 10 leaves per cm.

FLOWER

Flowering not observed.

OTHER CHARACTERISTICS

Disease and pest resistance: Neither resistance nor susceptibility observed.

Drought tolerance: No tolerance for drought.

Temperature tolerance: USDA Zones 5 to 9.

What is claimed is:

1. A new and distinct cultivar of *Thuja* plant named 'MonRig' as herein illustrated and described.

* * * * *